United States Patent
Okuyama et al.

(10) Patent No.: US 10,508,072 B2
(45) Date of Patent: Dec. 17, 2019

(54) METHOD FOR PRODUCING ACID HALIDE SOLUTION, MIXED SOLUTION, AND METHOD FOR PRODUCING MONOESTER COMPOUND

(71) Applicant: ZEON CORPORATION, Tokyo (JP)

(72) Inventors: Kumi Okuyama, Tokyo (JP); Kei Sakamoto, Tokyo (JP); Kanako Sanuki, Tokyo (JP); Hiroki Iwaki, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 15/761,541

(22) PCT Filed: Sep. 29, 2016

(86) PCT No.: PCT/JP2016/004401
§ 371 (c)(1),
(2) Date: Mar. 20, 2018

(87) PCT Pub. No.: WO2017/056501
PCT Pub. Date: Apr. 6, 2017

(65) Prior Publication Data
US 2018/0346401 A1     Dec. 6, 2018

(30) Foreign Application Priority Data
Oct. 2, 2015   (JP) ................ 2015-196700
Feb. 9, 2016   (JP) ................ 2016-022402

(51) Int. Cl.
*C07C 67/14*     (2006.01)

(52) U.S. Cl.
CPC .......... *C07C 67/14* (2013.01); *C07C 2601/14* (2017.05)

(58) Field of Classification Search
CPC ................................................ C07C 67/14
See application file for complete search history.

(56) References Cited

U.S. PATENT DOCUMENTS

| 5,663,432 A | 9/1997 | Villa et al. |
| 2015/0175564 A1* | 6/2015 | Sakamoto ............ C07D 417/12 526/257 |
| 2016/0024055 A1* | 1/2016 | Mischke .............. C07D 403/12 514/221 |

FOREIGN PATENT DOCUMENTS

| JP | H11505234 A | 5/1999 |
| JP | 2007314443 A | 12/2007 |
| WO | 2014010325 A1 | 1/2014 |

OTHER PUBLICATIONS

Van Waes, F.E.A., et al., Efficient and catalyst-free condensation of acid chlorides and alcohols using continuous flow, 2012, Green Chemistry, vol. 14, pp. 2776-2779 (Year: 2012).*
Apr. 3, 2018, International Preliminary Report on Patentability issued in the International Patent Application No. PCT/JP2016/004401.
Dec. 13, 2016, International Search Report issued in the International Patent Application No. PCT/JP2016/004401.
Kenneth A. Burdett, "An Improved Acid Chloride Preparation via Phase Transfer Catalysis," Synthesis, 1991, pp. 441-442.
Mar. 13, 2019, the Extended European Search Report issued by the European Patent Office in the corresponding European Patent Application No. 16850679.8.

* cited by examiner

*Primary Examiner* — Yate' K Cutliff
(74) *Attorney, Agent, or Firm* — Kenja IP Law PC

(57) ABSTRACT

The present disclosure provides a method for producing an acid halide solution that is useful as a production intermediate or the like that allows industrially advantageous production of a polymerizable liquid crystal compound. The method for producing an acid halide solution of the present disclosure includes a step α of reacting a halogenating agent and a dicarboxylic acid compound in a water-immiscible organic solvent in the presence of a tetraalkylammonium salt to obtain a water-immiscible organic solvent solution including an acid halide, and a step β of concentrating the obtained water-immiscible organic solvent solution.

8 Claims, No Drawings

METHOD FOR PRODUCING ACID HALIDE SOLUTION, MIXED SOLUTION, AND METHOD FOR PRODUCING MONOESTER COMPOUND

TECHNICAL FIELD

The present disclosure relates to a method for producing an acid halide solution that is useful as a production intermediate of a polymerizable liquid crystal compound, a mixed solution that includes a dicarboxylic acid halide, and a method for producing a monoester compound that uses the acid halide solution.

BACKGROUND

A monoester compound of cycloalkane dicarboxylic acid is a useful compound as, for example, a production intermediate of a liquid crystal material or an electron transport material; for example, see patent literature (PTL) 1.

The monoester compound is typically synthesized by reacting dicarboxylic acid chloride and a hydroxy compound.

A known method for producing dicarboxylic acid chloride is a method (acid halide method) to cause a chlorinating agent, such as thionyl chloride, to act on a dicarboxylic acid compound in the presence of a reaction catalyst such as N,N-dimethylformamide, triethylamine, or a tetraalkylammonium salt.

For example, PTL 2 discloses a method for producing 5-amino-2,4,6-triiodoisophthalic acid dichloride by reacting thionyl chloride with 5-amino-2,4,6-triiodoisophthalic acid in the presence of a tetraalkylammonium salt.

PTL 3 discloses a method for using the acid halide method to produce an ester group-containing tetracarboxylic acid dianhydride that has a predetermined structure. PTL 3 also discloses that when reacting thionyl chloride with dicarboxylic acid, N,N-dimethylformamide or pyridine may be added to the reaction system as catalysts.

Non-patent literature (NPL) 1 discloses a method for producing dicarboxylic acid dichloride by reacting thionyl chloride, in the presence of benzyltriethylammonium chloride, with dicarboxylic acid that has a predetermined structure.

CITATION LIST

Patent Literature

PTL 1: WO2014/010325
PTL 2: JP H11-505234 A
PTL 3: JP 2007-314443 A

Non-Patent Literature

NPL 1: A. Burdett, Synthesis, 1991, 441

SUMMARY

Technical Problem

In the case of reacting dicarboxylic acid chloride obtained with the aforementioned acid halide method with a hydroxy compound to produce a monoester compound, the dicarboxylic acid dichloride that is the raw material is isolated and then used. Specifically, the dicarboxylic acid chloride obtained by the acid halide method is used in the production of a monoester compound after being isolated by a recrystallization method or the like from the residue remaining after removing the solvent and low boiling point substances from the reaction solution yielded by reacting a dicarboxylic acid compound and a chlorinating agent such as thionyl chloride. The reason is that when acid components such as $SO_2$, HCl, and $SOCl_2$ derived from a chlorinating agent remain, the reaction yield during the subsequent esterification reaction significantly deteriorates, and therefore these acid components are completely removed before the esterification reaction.

However, while a purification method such as a recrystallization method can be adopted when producing a target substance on a small scale, a purification method such as a recrystallization method is complicated for production on an industrial scale and cannot be considered an industrially advantageous production method.

The present disclosure has been conceived in light of these circumstances, and an aim thereof is to provide a method for producing an acid halide solution, a mixed solution that includes a dicarboxylic acid halide, and a method for producing a monoester compound that uses the acid halide solution, which allow industrially advantageous production of a polymerizable liquid crystal compound.

Solution to Problem

In order to solve the problems described above, we conducted diligent investigation into an industrial production method for producing a dicarboxylic acid chloride by reacting a thionyl chloride with a dicarboxylic acid compound in the presence of a reaction catalyst and then producing a monoester compound using the resulting dicarboxylic acid chloride. We tested a method to concentrate the reaction solution containing the prepared acid chloride without drying the reaction solution and to perform the subsequent esterification reaction directly. As a result, we discovered that depending on the type of reaction catalyst used, the subsequent esterification reaction may or may not be adversely affected (i.e. the esterification reaction yield may or may not be reduced). We completed the present disclosure by generalizing this finding.

The present disclosure thus provides a method for producing an acid halide solution in [1] to [4] below, a mixed solution in [5] to [7], and a method for producing a monoester compound in [8] to [12].

[1] A method for producing an acid halide solution, the method comprising:

a step α of reacting a halogenating agent and a dicarboxylic acid compound represented by Formula (II) below in a water-immiscible organic solvent in the presence of a tetraalkylammonium salt represented by Formula (I) below to obtain a water-immiscible organic solvent solution including an acid halide compound represented by Formula (III) below, $$R^1R^2R^3R^4N^+A^-  \quad (I)$$

where in Formula (I), $A^-$ represents a halide ion or $R^5SO_3^-$, $R^5$ represents a methyl group, a phenyl group, or a 4-methyl phenyl group, $R^1$, $R^2$, $R^3$, and $R^4$ independently represent an alkyl group that is unsubstituted or has a substituent, and a total number of carbon atoms in $R^1$, $R^2$, $R^3$, and $R^4$ is at least 4 and no greater than 100,

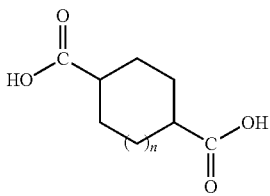

where in Formula (II), n represents 0 or 1,

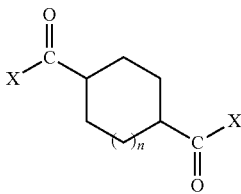

where in Formula (III), n represents 0 or 1, and X represents a halogen atom; and
a step β of concentrating the obtained water-immiscible organic solvent solution.

[2] The method for producing an acid halide solution of [1], wherein the halogenating agent is at least one selected from the group consisting of thionyl chloride, oxalyl chloride, sulfuryl chloride, phosphoryl chloride, phosphorus trichloride, and phosphorus pentachloride.

[3] The method for producing an acid halide solution of [1] or [2], wherein the tetraalkylammonium salt is at least one selected from the group consisting of benzyltrimethylammonium chloride, benzyltriethylammonium chloride, methyltrioctylammonium chloride, and tetrabutylammonium chloride.

[4] The method for producing an acid halide solution of any one of [1] to [3], wherein
the dicarboxylic acid compound represented by Formula (II) is a compound indicated by Formula (II-a) below,

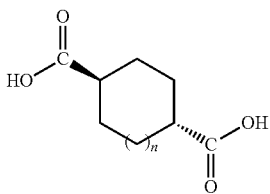

where in Formula (II-a), n represents 0 or 1.

[5] A mixed solution comprising:
a water-immiscible organic solvent;
a dicarboxylic acid chloride indicated by Formula (III-1) below,

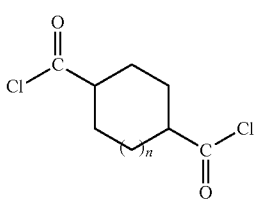

where in Formula (III-1), n represents 0 or 1, a tetraalkylammonium salt represented by Formula (I) below, $$R^1R^2R^3R^4N^+A^-$$ (I)

where in Formula (I), $A^-$ represents a halide ion or $R^5SO_3^-$, $R^5$ represents a methyl group, a phenyl group, or a 4-methyl phenyl group, $R^1$, $R^2$, $R^3$, and $R^4$ independently represent an alkyl group that is unsubstituted or has a substituent, and a total number of carbon atoms in $R^1$, $R^2$, $R^3$, and $R^4$ is at least 4 and no greater than 100, and
hydrochloric acid in an amount of at least 0.1 parts by mass and no greater than 3 parts by mass with respect to 100 parts by mass of the dicarboxylic acid chloride indicated by Formula (III-1).

[6] The mixed solution of [5], wherein the tetraalkylammonium salt is at least one selected from the group consisting of benzyltrimethylammonium chloride, benzyltriethylammonium chloride, methyltrioctylammonium chloride, and tetrabutylammonium chloride.

[7] The mixed solution of [5] or [6], wherein the dicarboxylic acid chloride is trans-1,4-cyclohexanedicarboxylic acid dichloride.

[8] A method for producing a monoester compound indicated by Formula (V) below,

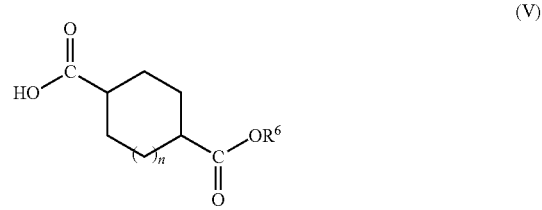

where in Formula (V), $R^6$ represents an organic group and n represents 0 or 1,
the method comprising:
a step γ of adding a base and a hydroxy compound indicated by Formula (IV), $R^6OH$, where in Formula (IV), $R^6$ represents the organic group, to an acid halide solution obtained by the method for producing an acid halide solution of any one of [1] to [4].

[9] The method for producing a monoester compound of [8], wherein the hydroxy compound indicated by Formula (IV) is a compound indicated by Formula (IV-1) below,

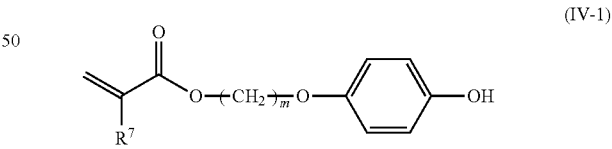

where in Formula (IV-1), $R^7$ represents a hydrogen atom, a methyl group, or a chlorine atom, and m is an integer of at least 1 and no greater than 20).

[10] The method for producing a monoester compound of [8] or [9], further comprising a step δ, after the step γ, of washing a reaction solution obtained in the step γ with a weakly acidic buffer solution.

[11] The method for producing a monoester compound of [10], wherein the weakly acidic buffer solution is an aqueous solution with a pH of at least 5.0 and no greater than 6.0.

[12] The method for producing a monoester compound of [10] or [11], wherein the weakly acidic buffer solution is an aqueous solution of a mixture of acetic acid and sodium acetate and/or an aqueous solution of a mixture of potassium hydrogen phthalate and sodium hydroxide.

Advantageous Effect

According to the present disclosure, a method for producing an acid halide solution that is useful as a production intermediate or the like that allows industrially advantageous production of a polymerizable liquid crystal compound, a mixed solution that contains a dicarboxylic acid halide, and a method for producing a monoester compound using the acid halide solution are provided.

DETAILED DESCRIPTION

The present disclosure is described below in detail in three sections: 1) method for producing an acid halide solution, 2) mixed solution, and 3) method for producing a monoester compound.

1) Method for Producing an Acid Halide Solution

The method for producing an acid halide solution according to the present disclosure includes a step α of reacting a halogenating agent and a dicarboxylic acid compound represented by Formula (II) (also referred to below as "dicarboxylic acid compound (II)") in a water-immiscible organic solvent in the presence of a tetraalkylammonium salt represented by Formula (I) (also referred to below as "tetraalkylammonium salt (I)") to obtain a water-immiscible organic solvent solution including an acid halide compound represented by Formula (III) (also referred to below as "acid halide compound (III)"), and a step β of concentrating the water-immiscible organic solvent solution obtained in step α. These steps are described in order below.

[Step α]

Step α is a step of reacting the dicarboxylic acid compound (II) and a halogenating agent in a water-immiscible organic solvent in the presence of the tetraalkylammonium salt (I) to obtain a water-immiscible organic solvent solution including the acid halide compound (III).

[Dicarboxylic Acid Compound (II)]

The dicarboxylic acid compound (II) used in the present disclosure is a dicarboxylic acid represented by Formula (II). In Formula (II), n represents 0 or 1 and is preferably 1.

Specific examples of the dicarboxylic acid compound (II) include 1,3-cyclopentanedicarboxylic acid and 1,4-cyclohexanedicarboxylic acid. Among these, 1,4-cyclohexanedicarboxylic acid is preferred in terms of usefulness as the raw material for producing a polymerizable liquid crystal compound.

A cis-trans stereoisomer may exist in the dicarboxylic acid compound (II), as indicated by Formulas (II-1) and (II-2) below. In the present disclosure, any of a cis isomer, a trans isomer, or a cis-trans isomer mixture (racemate) can be used. Among these, the trans isomer represented by Formula (II-1) below is preferred in terms of usefulness as a production intermediate or the like of a polymerizable liquid crystal compound.

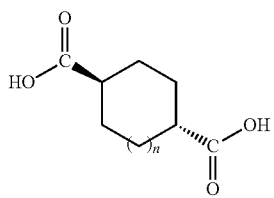

(II-1)

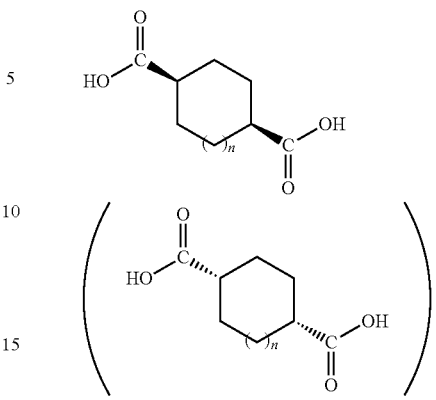

(II-2)

[Water-Immiscible Organic Solvent]

The water-immiscible organic solvent used in the present disclosure is not particularly limited, as long as it is an organic solvent that is immiscible with water and that dissolves the dicarboxylic acid compound (II) and the acid halide compound (III) that corresponds to the dicarboxylic acid compound (II). An example of an organic solvent that is immiscible with water is an organic solvent having a solubility of no greater than 10 g/L in water at 25° C.

Specific examples of the water-immiscible organic solvent include ester solvents such as ethyl acetate, propyl acetate, and butyl acetate; halogenated hydrocarbon solvents such as dichloromethane, 1,2-dichloroethane, chloroform, carbon tetrachloride, chlorobenzene, and o-dichlorobenzene; ether solvents such as diethyl ether, dibutyl ether, diisopropyl ether, ethylene glycol dimethyl ether, cyclopentyl methyl ether, methyl-t-butyl ether, and 1,2-dimethoxyethane; chain aliphatic hydrocarbon solvents such as n-pentane, n-hexane, and n-heptane; aromatic hydrocarbon solvents such as benzene, toluene, and xylene; alicyclic hydrocarbon solvents such as cyclopentane and cyclohexane; and ketone solvents such as 2-butanone.

These solvents may be used alone or in combination.

Among these solvents, halogenated hydrocarbon solvents, ether solvents, and aromatic hydrocarbon solvents are preferred, and cyclopentyl methyl ether, chloroform, and toluene are more preferred.

As the water-immiscible organic solvent, an organic solvent for which the Hildebrand solubility parameter is at least 14.0 $MPa^{1/2}$ and no greater than 22.0 $MPa^{1/2}$ is preferred. The Hildebrand solubility parameter is a value (δ), defined by the regular solution theory introduced by Hildebrand, that provides a numerical estimate of the degree of interaction between materials.

Using such an organic solvent facilitates operation during the subsequent washing step δ and makes it possible to obtain the target monoester compound efficiently.

Preferred examples of the water-immiscible organic solvent include ether solvents such as cyclopentyl methyl ether (Hildebrand solubility parameter (δ): 17.2 $MPa^{1/2}$), methyl-t-butyl ether ((δ): 15.6 $MPa^{1/2}$), diethyl ether ((δ): 15.1 $MPa^{1/2}$), dibutyl ether ((δ): 14.9 $MPa^{1/2}$), diisopropyl ether ((δ): 14.1 $MPa^{1/2}$), and 1,2-dimethoxyethane ((δ): 19.2 $MPa^{1/2}$); halogenated hydrocarbon solvents such as chloroform ((δ): 19.0 $MPa^{1/2}$); ester solvents such as ethyl acetate ((δ): 18.6 $MPa^{1/2}$); aromatic hydrocarbon solvents such as toluene ((δ): 18.2 $MPa^{1/2}$); alicyclic hydrocarbon solvents such as cyclohexane ((δ): 16.7 $MPa^{1/2}$); ketone solvents such as 2-butanone (($\delta$): 19.0 MPa$^{1/2}$); and mixed solvents thereof. In the case of using a mixed solvent, the solubility parameter of the mixed solvent can be calculated by the addition rule.

The amount of water-immiscible organic solvent used is normally at least 0.1 g and no greater than 100 g, preferably at least 0.5 g and no greater than 50 g, per 1 g of the dicarboxylic acid compound (II).

[Tetraalkylammonium Salt (I)]

In the present disclosure, the tetraalkylammonium salt (I) is used as a reaction catalyst when reacting the dicarboxylic acid compound (II) and the halogenating agent to obtain the dicarboxylic acid halide corresponding to the dicarboxylic acid compound (II).

By using the tetraalkylammonium salt (I) as a reaction catalyst, the target dicarboxylic acid halide can be obtained using less of the catalyst, at a lower reaction temperature, in a shorter time, and with a better yield. When using the acid halide solution as is as the raw material for producing for the next esterification reaction, the tetraalkylammonium salt (I) does not often have an adverse effect on the esterification reaction in the subsequent step (such as lowering the yield of the esterification reaction).

In Formula (I), A$^-$ represents a halide ion such as a chloride ion or bromide ion, or a sulfonate ion represented by the formula R$^5$SO$_3^-$. Here, R$^5$ represents a methyl group, a phenyl group, or a 4-methyl phenyl group.

Among these, a halide ion is preferred as A$^-$ from the perspective of versatility, and a chloride ion is particularly preferred.

In Formula (I), R$^1$, R$^2$, R$^3$, and R$^4$ independently represent an alkyl group that is unsubstituted or has a substituent.

Examples of the alkyl group that is unsubstituted or has a substituent in R$^1$, R$^2$, R$^3$, and R$^4$ include an alkyl group having at least 1 and no greater than 30 carbon atoms, preferably an alkyl group having at least 1 and no greater than 20 carbon atoms, and more preferably an alkyl group having at least 1 and no greater than 18 carbon atoms. The alkyl group of R$^1$, R$^2$, R$^3$, and R$^4$ may have a linear structure or a branched structure.

Specific examples of the alkyl group that is unsubstituted or has a substituent in R$^2$, R$^3$, and R$^4$ include a methyl group, an ethyl group, an n-propyl group, an isopropyl group, an n-butyl group, an isobutyl group, a sec-butyl group, a t-butyl group, an n-pentyl group, an isoamyl group, an n-hexyl group, an n-heptyl group, an n-octyl group, an n-nonyl group, an n-decyl group, an n-undecyl group, an n-dodecyl group, and a cetyl group.

However, the total number of carbon atoms in R$^2$, R$^3$, and R$^4$ is at least 4 and no greater than 100, preferably at least 4 and no greater than 80, more preferably at least 4 and no greater than 50, and particularly preferably at least 4 and no greater than 30.

The alkyl group of R$^1$, R$^2$, R$^3$, and R$^4$ can have any substituent that is a group inert to the reaction. Examples include an alkoxy group having at least 1 and no greater than 10 carbon atoms, such as a methoxy group, an ethoxy group, a propoxy group, or a butoxy group; and a phenyl group that is unsubstituted or has a substituent, such as a phenyl group, a 2-chlorophenyl group, a 4-methylphenyl group, and a phenethyl group.

Specific examples of the alkyl group that has a substituent include a 2-methoxyethyl group, a 3-methoxypropyl group, a benzyl group, a 4-methylbenzyl group, and a phenethyl group, but the alkyl group that has a substituent is not limited to these examples.

Preferred examples of the tetraalkylammonium salt (I) include benzyltrimethylammonium chloride, benzyltriethylammonium chloride, methyltrioctylammonium chloride, and tetrabutylammonium chloride.

One type of the tetraalkylammonium salt (I) may be used alone, or two or more types may be used in combination.

To better obtain the effects of the present disclosure, the amount of tetraalkylammonium salt (I) used is preferably at least 0.0001 mol, more preferably at least 0.001 mol, preferably no greater than 1 mol, and more preferably no greater than 0.5 mol per 1 mol of the dicarboxylic acid compound (II).

[Halogenating Agent]

As the halogenating agent used in the present disclosure, any halogenating agent that converts the dicarboxylic acid compound (II) to the corresponding acid halide compound (III) may be used.

Examples of the halogenating agent that is used include chlorinating agents such as thionyl chloride (SOCl$_2$), oxalyl chloride [(COCl)$_2$], sulfuryl chloride (SO$_2$Cl$_2$), phosphoryl chloride (POCl$_3$), phosphorus trichloride (PCl$_3$), and phosphorus pentachloride (PCl$_5$); and brominating agents such as thionyl bromide (SOBr$_2$), boron tribromide (BBr$_3$), and bromine (Br$_2$).

These halogenating agents may be used alone or in combination.

Among these halogenating agents, at least one selected from the group consisting of thionyl chloride, oxalyl chloride, sulfuryl chloride, phosphoryl chloride, phosphorus trichloride, and phosphorus pentachloride is preferred from the perspective of versatility.

The amount of halogenating agent used is normally at least 2 mol and no greater than 5 mol, preferably at least 2 mol and no greater than 3 mol, per 1 mol of the dicarboxylic acid compound (II).

The method for reacting the dicarboxylic acid compound (II) and the halogenating agent is not particularly limited. For example, after adding a predetermined amount of the tetraalkylammonium salt (I) to a water-immiscible organic solvent solution including the dicarboxylic acid compound (II), a predetermined amount of the halogenating agent may be added, with the whole solution then being stirred.

The reaction temperature is normally at least 0° C. and no greater than 100° C., preferably at least 0° C. and no greater than 50° C.

While the reaction time also depends on factors such as the type of substrate and the reaction scale, the reaction time is normally from several minutes to 8 hours.

[Acid Halide Compound (III)]

The acid halide compound (III) generated in step α is the dicarboxylic acid halide represented by Formula (III). In Formula (III), n represents 0 or 1 and is preferably 1. In Formula (III), X represents a halogen atom and is preferably a chlorine atom.

The acid halide compound (III) corresponds to the dicarboxylic acid compound (II). Accordingly, n in Formula (II) and n in Formula (III) are normally equivalent. X is a halogen atom derived from a halogenating agent.

[Step β]

Step β is a step of concentrating the water-immiscible organic solvent solution obtained in step α. By providing step β, the acid component derived from the halogenating agent and remaining in the reaction system (SO$_2$, HCl, SOCl$_2$, or the like) can be removed.

In the present disclosure, "concentrating" refers to an operation to remove the acid component derived from the halogenating agent (SO$_2$, HCl, SOCl$_2$, or the like) along with solvent from the reaction solution (water-immiscible organic solvent solution) obtained in step α and does not refer to completely removing the solvent in the water-immiscible organic solvent solution. Normally, the water-immiscible organic solvent solution is concentrated until the amount of solvent in the water-immiscible organic solvent solution is, by mass ratio, at least 1/10 and no greater than 4/5, preferably at least 1/10 and no greater than 1/2, of the initial (at the start of step α) amount of solvent (charge amount).

The concentration method is not particularly limited, and examples include an evaporation concentration method using an evaporation concentration apparatus, such as an evaporator.

The concentration operation may be performed under normal pressure (approximately 0.1 MPa) or under reduced pressure. The concentration operation is preferably performed under reduced pressure, since doing so can remove the acid component efficiently. In the case of concentrating under reduced pressure, the pressure reduction is normally at least 10 mmHg and no greater than 500 mmHg.

In the above-described way, a concentrated solution of the water-immiscible organic solvent solution can be obtained.

The obtained concentrated solution is an acid halide solution that includes the acid halide compound (III). This acid halide solution normally includes a water-immiscible organic solvent, the acid halide compound (III), the tetraalkylammonium salt (I), and an acid component derived from a halogenating agent and optionally further includes an unreacted halogenating agent. The amount of the acid component derived from the halogenating agent in the acid halide solution is normally at least 0.1 parts by mass and no greater than 3 parts by mass per 100 parts by mass of the acid halide compound (III).

As described below, this acid halide solution is useful as a raw material for producing a monoester compound by an esterification reaction with a hydroxy compound.

2) Mixed Solution

The mixed solution of the present disclosure is a concentrated solution of a water-immiscible organic solvent solution obtained by the above-described method for producing an acid halide solution. In this mixed solution, the acid halide compound (III) is the dicarboxylic acid chloride represented by Formula (III-1) (also referred to below as "dicarboxylic acid chloride (III-1)"), and the content of the hydrochloric acid as an acid component is low.

In other words, the mixed solution according to the present disclosure includes a water-immiscible organic solvent, the dicarboxylic acid chloride (III-1), the tetraalkylammonium salt (I), and a small amount of hydrochloric acid.

In the mixed solution according to the present disclosure, the water-immiscible organic solvent is preferably a halogenated hydrocarbon solvent, an ether solvent, or an aromatic hydrocarbon solvent and is more preferably cyclopentyl methyl ether, chloroform, or toluene.

In the mixed solution according to the present disclosure, the tetraalkylammonium salt (I) is preferably one or more selected from the group consisting of benzyltrimethylammonium chloride, benzyltriethylammonium chloride, methyltrioctylammonium chloride, and tetrabutylammonium chloride.

Furthermore, in the mixed solution of the present disclosure, the dicarboxylic acid chloride (III-1) is preferably 1,4-cyclohexanedicarboxylic acid dichloride and is particularly preferably trans-1,4-cyclohexanedicarboxylic acid dichloride.

The amount of the hydrochloric acid in the mixed solution is normally at least 0.1 parts by mass and no greater than 3 parts by mass per 100 parts by mass of the dicarboxylic acid chloride (III-1). The amount of the hydrochloric acid in the mixed solution can be measured by the method listed in the Examples.

The mixed solution according to the present disclosure is particularly useful as a raw material for producing the below-described monoester compound.

3) Method for Producing a Monoester Compound

The method for producing a monoester compound according to the present disclosure includes a step γ of adding a base and a hydroxy compound (also referred to below as "hydroxy compound (IV)") represented by Formula (IV), $R^6OH$, where $R^6$ represents an organic group, to an acid halide solution obtained by the above-described method for producing an acid halide solution according to the present disclosure.

An example of a reaction scheme of the method for producing a monoester compound according to the present disclosure is illustrated below. The case of X in the acid halide compound (III) included in the acid halide solution being a chlorine atom, i.e. the case of the acid halide compound (III) being dicarboxylic acid chloride (III-1) is illustrated below, but the present disclosure is not limited to the following example.

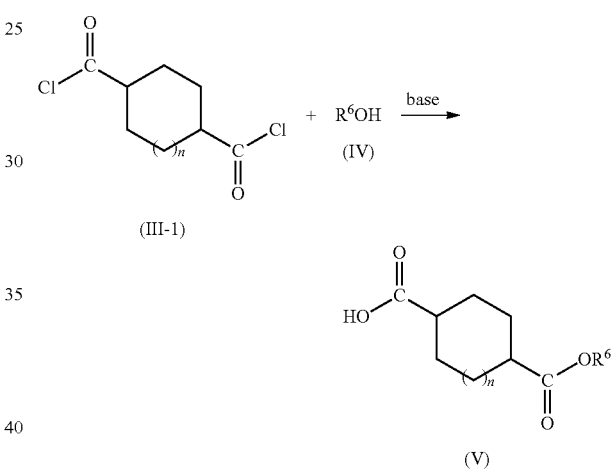

In other words, in the method for producing a monoester compound according to the present disclosure, an acid halide compound represented by Formula (III) (dicarboxylic acid chloride (III-1) in the above example) and a hydroxy compound represented by Formula (IV) are reacted to obtain a monoester compound represented by Formula (V) (also referred to below as "monoester compound (V)"). The unreacted acid halide portion (the acid chloride portion on the left side in the above example) is hydrolyzed during processing of the obtained reaction solution and transformed into a carboxyl group.

Here, $R^6$ in Formula (IV) and (V) represent an organic group. The organic group represented by $R^6$ is a group bonded by a carbon atom to an oxygen atom of a hydroxy group or the like.

The number of carbon atoms in the organic group represented by $R^6$ is not particularly limited but is preferably at least 1 and no greater than 30.

Examples of the organic group include an aliphatic hydrocarbon group that is unsubstituted or has a substituent, such as an alkyl group, having at least 1 and no greater than 30 carbon atoms, that is unsubstituted or has a substituent, an alkenyl group, having at least 2 and no greater than 30 carbon atoms, that is unsubstituted or has a substituent, an alkynyl group, having at least 2 and no greater than 30 carbon atoms, that is unsubstituted or has a substituent, and a cycloalkyl group, having at least 3 and no greater than 30 carbon atoms, that is unsubstituted or has a substituent; an aromatic hydrocarbon group, having at least 6 and no greater than 30 carbon atoms, that is unsubstituted or has a substituent, and an aromatic heterocyclic group, having at least 1 and no greater than 30 carbon atoms, that is unsubstituted or has a substituent.

In Formula (V), n represents 0 or 1 and is preferably 1. The monoester compound (V) is the result of monoesterification of the acid halide compound (III). Accordingly, n in Formula (III) and n in Formula (V) are normally equivalent.

The hydroxy compound (IV) used in the present disclosure may be an alcohol compound in which $R^6$ is an aliphatic hydrocarbon group that is unsubstituted or has a substituent, or may be a phenolic compound in which $R^6$ is an aromatic hydrocarbon group, having at least 6 and no greater than 30 carbon atoms, that is unsubstituted or has a substituent, or in which $R^6$ is an aromatic heterocyclic group, having at least 1 and no greater than 30 carbon atoms, that is unsubstituted or has a substituent. In the present disclosure, in terms of usefulness as a production intermediate or the like of a polymerizable liquid crystal compound, the hydroxy compound (IV) is preferably a phenolic compound, is more preferably a phenol compound in which $R^6$ is an aromatic hydrocarbon group, having at least 6 and no greater than 30 carbon atoms, that is unsubstituted or has a substituent, and is particularly preferably the compound represented by Formula (IV-1) below.

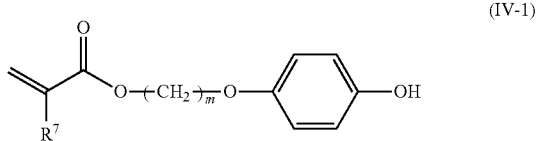

(IV-1)

Here, in Formula (IV-1), $R^7$ represents a hydrogen atom, a methyl group, or a chlorine atom.

Furthermore, m represents an integer of at least 1 and no greater than 20, preferably an integer of at least 1 and no greater than 12, and more preferably an integer of at least 2 and no greater than 10.

The compound represented by Formula (IV-1) is a commonly known substance and can be produced and acquired with commonly known conventional methods (for example, see WO2014/010325).

Examples of the base used in the present disclosure include organic bases such as triethylamine, diisopropylethylamine, phenyldimethylamine, pyridine, picoline, lutidine, and 4-(dimethylamino)pyridine; and inorganic bases such as sodium hydroxide, potassium hydroxide, magnesium hydroxide, calcium hydroxide, sodium carbonate, and potassium carbonate. Any one of such bases can be used individually or any two or more of such bases can be used in combination.

Among these bases, organic bases are preferable, tertiary amines such as triethylamine and diisopropylethylamine are more preferable, and triethylamine is particularly preferable in terms of the target substance being obtained with a good yield.

The amount of base used is normally at least 1 mol and no greater than 3 mol, preferably at least 1 mol and no greater than 1.5 mol, per 1 mol of the acid halide compound (III).

The esterification reaction may, for example, be carried out by adding the hydroxy compound (IV) to a water-immiscible organic solvent solution of the acid halide compound (III), adding a base to the resulting reaction mixture, and stirring the entire reaction mixture.

The reaction temperature is normally at least 0° C. and no greater than 80° C., preferably at least 0° C. and no greater than 50° C., and more preferably at least 0° C. and no greater than 30° C.

While the reaction time also depends on factors such as the reaction scale, the reaction time is normally from several minutes to several hours.

The production method of the present disclosure preferably includes a step δ, after step γ, of washing a reaction solution obtained in the step γ with a weakly acidic buffer solution (typically a buffer solution having a pH of at least 4.5 and less than 7), preferably a buffer solution having a pH of at least 5.0 and no greater than 6.0, and more preferably a buffered aqueous solution having a pH of at least 5.0 and no greater than 6.0.

In the reaction solution obtained by step γ, a substance derived from the acid halide compound (III) that is the raw material (a dicarboxylic acid compound (II) generated by hydrolysis of the unreacted acid halide compound (III)) is normally included in addition to the target substance, but by providing this step δ, the content of the dicarboxylic acid compound (II) in the reaction solution can be reduced. Consequently, in the reaction in subsequent steps, an adverse effect due to the dicarboxylic acid compound (II) (a reduction in yield due to the occurrence of a side reaction) can be prevented.

The buffer solution is a solution having a buffering effect on the hydrogen ion concentration and is typically obtained by mixing a weak acid and its conjugate base or a weak base and its conjugate acid. By using a buffer solution, decomposition of the target substance due to a sudden change in pH can be prevented, thereby obtaining the target substance with a good yield.

Examples of the buffer solution usable in the present disclosure include mixed system buffer solutions, such as a combination of acetic acid and sodium acetate, a combination of potassium hydrogen phthalate and sodium hydroxide, a combination of potassium dihydrogen phosphate and sodium hydroxide, a combination of sodium citrate and sodium hydroxide, and a combination of potassium dihydrogen phosphate and citric acid.

Among these, a mixed system buffer solution of acetic acid and sodium acetate or a mixed system buffer solution of potassium hydrogen phthalate and sodium hydroxide is preferable in terms of better obtaining the effects of the present disclosure.

The buffer solution can be adjusted by commonly known conventional methods. For example, a mixed system buffer solution, having a pH of 5.6 (18° C.), of acetic acid and sodium acetate can be adjusted by mixing 0.2 N acetic acid and a 0.2 M sodium acetate aqueous solution at a ratio of 1.9 ml of the 0.2 N acetic acid and 18.1 ml of the 0.2 M sodium acetate aqueous solution. A mixed system buffer solution, having a pH of 5.8 (20° C.), of potassium hydrogen phthalate and sodium hydroxide can be adjusted by mixing a 0.2 M potassium hydrogen phthalate aqueous solution, a 0.2 N sodium hydroxide aqueous solution, and water at a ratio of 50.0 ml of the 0.2 M potassium hydrogen phthalate aqueous solution, 43.0 ml of the 0.2 N sodium hydroxide aqueous solution, and 107.0 ml of the water.

The number of times the reaction solution is washed with the buffer solution in step δ is not particularly limited but is normally at least once and no more than three times. Washing in the buffer solution may take place after the reaction solution is washed with water.

The monoester compound (V) obtained in the above way is, for example, useful as the raw material for producing the polymerizable liquid crystal compound represented by Formula (5) below (for example, see WO2014/010325).

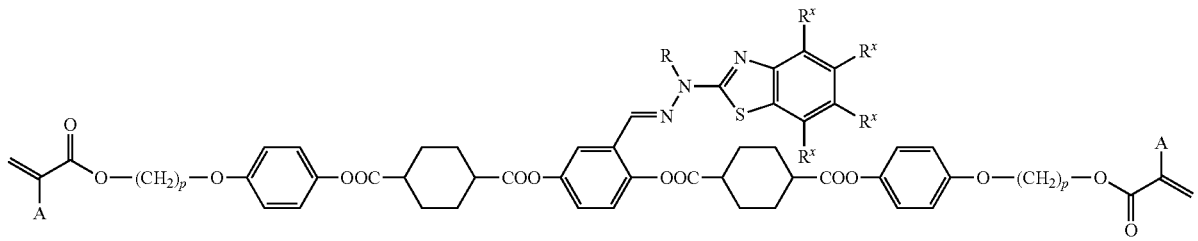

(5)

(In Formula (5), A represents a hydrogen atom, a methyl group, or a chlorine atom, R represents a hydrogen atom or an organic group having at least 1 and no greater than 20 carbon atoms, each $R^x$ independently represents a hydrogen atom, a halogen atom, an alkyl group having at least 1 and no greater than 6 carbon atoms, a cyano group, a nitro group, a fluoroalkyl group having at least 1 and no greater than 6 carbon atoms, an alkoxy group having at least 1 and no greater than 6 carbon atoms, or —C(=O)—O—$R^a$. Here, $R^a$ represents a hydrogen atom or an alkyl group, having at least 1 and no greater than 10 carbon atoms, that may have a substituent, and p represents an integer of at least 1 and no greater than 20.

The polymerizable liquid crystal compound represented by Formula (5) can, for example, be produced by the following steps.

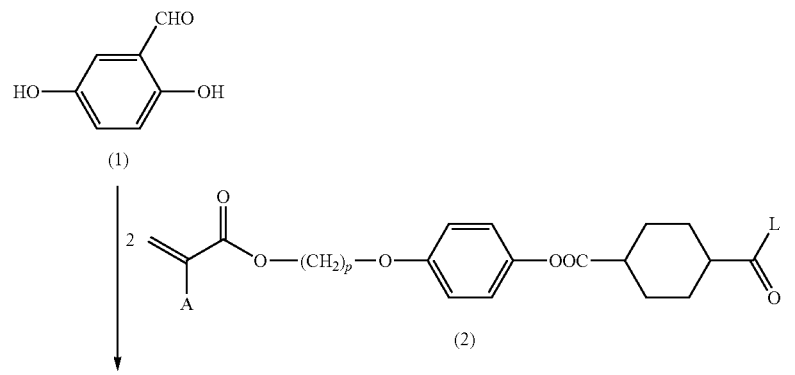

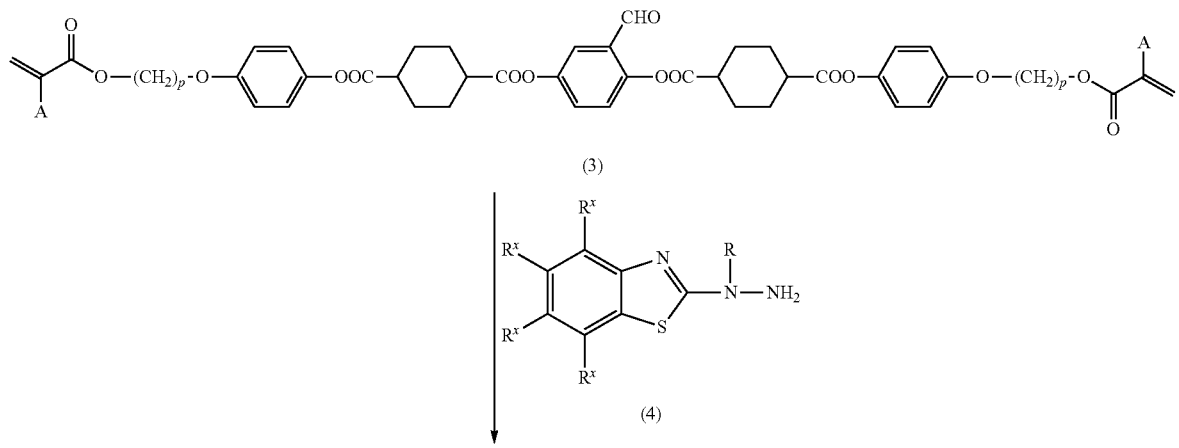

-continued

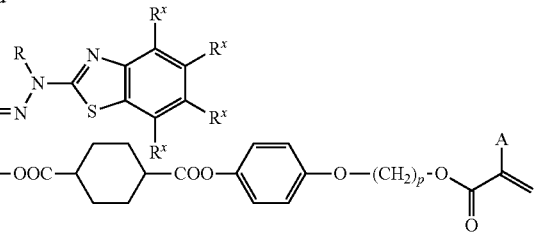

(5)

(In the Formula, A, R, $R^x$, and p have the same meaning as above. L represents a leaving group, such as a hydroxy group, a halogen atom, an alkylsulfonyloxy group, or an arylsulfonyloxy group.)

In other words, by reacting the aldehyde compound indicated by Formula (1) and the carboxylic acid monoester indicated by Formula (2) as a monoester compound (V), the compound indicated by Formula (3) can be obtained. Furthermore, by reacting the compound indicated by Formula (3) and the hydrazine compound indicated by Formula (4), the target polymerizable liquid crystal compound indicated by Formula (5) can be obtained.

In all of the reactions, the reaction temperature is normally at least 0° C. and no greater than 80° C., preferably at least 5° C. and no greater than 50° C., and more preferably at least 5° C. and no greater than 30° C. While the reaction time also depends on factors such as the reaction scale, the reaction time is normally from several minutes to several hours.

EXAMPLES

The present disclosure is described below in further detail through examples. However, the examples are in no way limiting.

(Example 1) Preparation of a Solution in which Dicarboxylic Acid Chloride and Benzyltrimethylammonium Chloride are Dissolved in Cyclopentyl Methyl Ether (CPME)

To a 3-neck reaction vessel equipped with a thermometer, 8.65 g (50.2 mmol) of trans-1,4-cyclohexane dicarboxylic acid as the dicarboxylic acid compound (II) and 86.5 g of CPME as a water-immiscible organic solvent were added in a nitrogen stream. Then, 47 mg (0.25 mmol) of benzyltrimethylammonium chloride as the tetraalkylammonium salt (I) was added. Subsequently, 12.54 g (105 mmol) of thionyl chloride as a halogenating agent was slowly added dropwise over 5 minutes at 23° C. After completion of the dropwise addition, the entire content was heated to 50° C. and was further stirred for one hour. After completion of the reaction, the result was concentrated with a rotary evaporator, and 80% (69 g) of the CPME that was used was extracted to prepare a solution in which dicarboxylic acid chloride (trans-1,4-cyclohexane dicarboxylic acid dichloride) and benzyltrimethylammonium chloride were dissolved in CPME. This solution was referred to as acid chloride solution (A).

(Example 2) Preparation of a Solution in which Dicarboxylic Acid Chloride and Tri(n-Octyl)Methylammonium Chloride are Dissolved in CPME A similar operation to that of Example 1 was performed, except for changing the 47 mg (0.25 mmol) of benzyltrimethylammonium chloride in Example 1 to 126 mg (0.25 mmol) of tri(n-octyl)methylammonium chloride (product name: Aliquat), to prepare a solution in which trans-1,4-cyclohexane dicarboxylic acid dichloride and tri(n-octyl)methylammonium chloride were dissolved in CPME. This solution was referred to as acid chloride solution (B).

(Example 3) Preparation of a Solution in which Dicarboxylic Acid Chloride and a Methyltrioctylammonium Chloride Mixture are Dissolved in CPME A similar operation to that of Example 1 was performed, except for changing the 47 mg (0.25 mmol) of benzyltrimethylammonium chloride in Example 1 to 126 mg (0.25 mmol) of a methyltrioctylammonium chloride mixture (product name: Adogen), to prepare a solution in which trans-1,4-cyclohexane dicarboxylic acid dichloride and a methyltrioctylammonium chloride mixture were dissolved in CPME. This solution was referred to as acid chloride solution (C).

(Example 4) Preparation of a Solution in which Dicarboxylic Acid Chloride and Benzyltrimethylammonium Chloride are Dissolved in Chloroform A similar operation to that of Example 1 was performed, except for changing the water-immiscible organic solvent from 86.5 g of CPME in Example 1 to 100 g of chloroform to prepare a solution in which trans-1,4-cyclohexane dicarboxylic acid dichloride and benzyltrimethylammonium chloride were dissolved in chloroform. This solution was referred to as acid chloride solution (D).

(Example 5) Preparation of a Solution in which Dicarboxylic Acid Chloride and Tri(n-Octyl)Methylammonium Chloride are Dissolved in Chloroform A similar operation to that of Example 2 was performed, except for changing the water-immiscible organic solvent from 86.5 g of CPME in Example 2 to 100 g of chloroform to prepare a solution in which trans-1,4-cyclohexane dicarboxylic acid dichloride and tri(n-octyl)methylammonium chloride were dissolved in chloroform. This solution was referred to as acid chloride solution (E).

(Example 6) Preparation of a Solution in which Dicarboxylic Acid Chloride and a Methyltrioctylammonium Chloride Mixture are Dissolved in Chloroform A similar operation to that of Example 3 was performed, except for changing the water-immiscible organic solvent from 86.5 g of CPME in Example 3 to 100 g of chloroform to prepare a solution in which trans-1,4-cyclohexane dicarboxylic acid dichloride and a methyltrioctylammonium chloride mixture were dissolved in chloroform. This solution was referred to as acid chloride solution (F).

(Example 7) Preparation of a Solution in which Dicarboxylic Acid Chloride and Tri(n-Octyl)Methylammonium Chloride are Dissolved in CPME A similar operation to that of Example 1 was performed, except for changing the 47 mg (0.25 mmol) of benzyltrimethylammonium chloride in Example 1 to 2.52 g (5.0 mmol) of tri(n-octyl)methylammonium chloride (product name: Aliquat) and changing the reaction time to 30 min, to prepare a solution in which trans-1,4-cyclohexane dicarboxylic acid dichloride and tri(n-octyl)methylammonium chloride were dissolved in CPME. This solution was referred to as acid chloride solution (G).

(Example 8) Production of Mixture 1

To a 3-neck reaction vessel equipped with a thermometer, the acid chloride solution (A) produced in Example 1 was added in a nitrogen stream, 235 g of CPME was then added, and the reaction vessel was immersed in an ice bath to achieve an internal temperature of 0° C. in the reaction solution. Then, 12.64 g (47.83 mmol) of 4-(6-acryloyloxy-hex-1-yloxy)phenol (produced by DKSH) as a hydroxy compound (IV) was added. Next, 5.08 g (50.2 mmol) of triethylamine as a base was slowly added dropwise over 5 minutes while maintaining the internal temperature of the reaction solution at 10° C. or lower. After completion of the dropwise addition, the entire content was further stirred for one hour at 0° C. A monoester and a diester were generated by the reaction shown below.

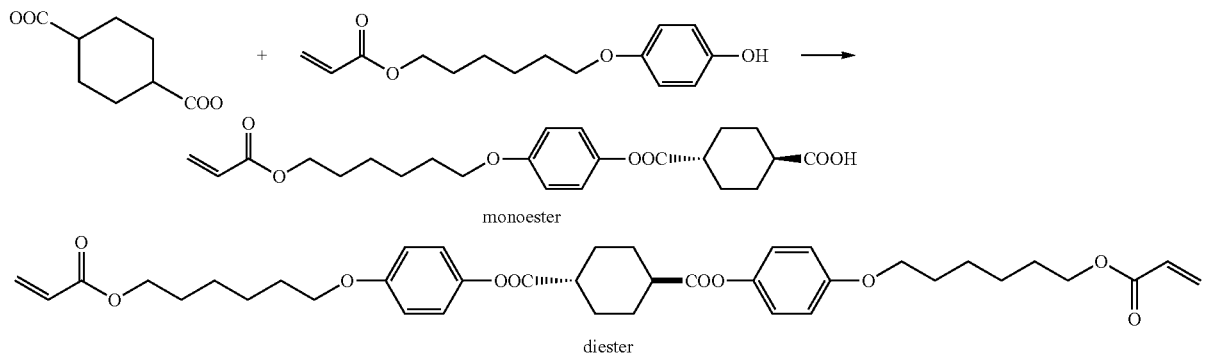

Next, 32 g of distilled water was added to the obtained reaction solution, the result was washed for 2 hours at 25° C., and the aqueous layer was then removed. The organic layer was washed three times with 53 g of a buffer solution (pH: 5.5) composed of an aqueous solution of a mixture of acetic acid and sodium acetate at a concentration of 1 mol/L, after which the buffer solution was extracted.

Subsequently, washing was performed once with 32 g of distilled water. To the obtained organic layer, 320 ml of n-hexane was added to cause crystals to precipitate, and the precipitated crystals were collected by filtration. After washing the obtained crystals with n-hexane, the crystals were vacuum dried, yielding 15.22 g of Mixture 1 as a white solid. The obtained crystals were analyzed by high performance liquid chromatography (HPLC), and the quantities of monoester and diester were measured with a calibration curve, revealing that 10.55 g (25.22 mmol) of the target monoester and 4.67 g (7.02 mmol) of diester were included.

(Example 9) Production of Mixture 2

A similar operation to that of Example 8 was performed, except for changing Example 8 by using the acid chloride solution (B) produced in Example 2 instead of the acid chloride solution (A) produced in Example 1. As a result, 15.45 g of a white solid was obtained. Confirming the composition with a similar method as for Example 8 revealed that 10.69 g (25.54 mmol) of the target monoester and 4.76 g (7.17 mmol) of diester were included.

(Example 10) Production of Mixture 3

A similar operation to that of Example 8 was performed, except for changing Example 8 by using the acid chloride solution (C) produced in Example 3 instead of the acid chloride solution (A) produced in Example 1. As a result, 14.93 g of a white solid was obtained. Confirming the composition with a similar method as for Example 8 revealed that 10.31 g (24.63 mmol) of the target monoester and 4.62 g (6.70 mmol) of diester were included.

(Example 11) Production of Mixture 4

To a 3-neck reaction vessel equipped with a thermometer, the acid chloride solution (D) produced in Example 4 was added in a nitrogen stream, after which 235 g of chloroform was added, and the reaction vessel was immersed in an ice bath to achieve an internal temperature of 0° C. in the reaction liquid. Then, 12.64 g (47.83 mmol) of 4-(6-acryloyloxy-hex-1-yloxy)phenol (produced by DKSH) as a hydroxy compound (IV) was added. Next, 5.08 g (50.2 mmol) of triethylamine as a base was slowly added dropwise over 5 minutes while maintaining the internal temperature of the reaction solution at 10° C. or lower. After completion of the dropwise addition, the entire content was further stirred for one hour at 0° C.

Next, 32 g of distilled water was added to the obtained reaction solution, the result was washed for 2 hours at 25° C., and the aqueous layer was then removed. The organic layer was washed three times with 53 g of a buffer solution (pH: 5.5) composed of an aqueous solution of a mixture of acetic acid and sodium acetate at a concentration of 1 mol/L, after which the buffer solution was extracted.

Subsequently, washing was performed once with 32 g of distilled water. To the obtained organic layer, 320 ml of n-hexane was added to cause crystals to precipitate, and the precipitated crystals were collected by filtration. After washing the obtained crystals with n-hexane, the crystals were vacuum dried, yielding 15.34 g of Mixture 4 as a white solid. Confirming the composition with a similar method as for Example 8 revealed that 10.20 g (24.36 mmol) of the target monoester and 5.14 g (7.74 mmol) of diester were included.

(Example 12) Production of Mixture 5

A similar operation to that of Example 11 was performed, except for changing Example 11 by using the acid chloride solution (E) produced in Example 5 instead of the acid chloride solution (D) produced in Example 4. As a result, 15.41 g of a white solid was obtained. Confirming the composition with a similar method as for Example 8 revealed that 10.21 g (24.40 mmol) of the target monoester and 5.20 g (7.83 mmol) of diester were included.

(Example 13) Production of Mixture 6

A similar operation to that of Example 11 was performed, except for changing Example 11 by using the acid chloride solution (F) produced in Example 6 instead of the acid chloride solution (D) produced in Example 4. As a result, 15.51 g of a white solid was obtained. Confirming the composition with a similar method as for Example 8 revealed that 10.34 g (24.71 mmol) of the target monoester and 5.17 g (7.78 mmol) of diester were included.

(Example 14) Production of Mixture 7

A similar operation to that of Example 8 was performed, except for changing Example 8 by using the acid chloride solution (G) produced in Example 7 instead of the acid chloride solution (A) produced in Example 1 and by changing the 5.08 g of triethylamine (50.2 mmol) to 6.10 g of triethylamine (60.2 mmol). As a result, 15.14 g of a white solid was obtained. Confirming the composition with a similar method as for Example 8 revealed that 10.35 g (24.72 mmol) of the target monoester and 4.79 g (7.21 mmol) of diester were included.

(Example 15) Preparation of a Solution in which Dicarboxylic Acid Chloride and Benzyltriethylammonium Chloride are Dissolved in CPME A similar operation to that of Example 1 was performed, except for changing the 47 mg (0.25 mmol) of benzyltrimethylammonium chloride in Example 1 to 57 mg (0.25 mmol) of benzyltriethylammonium chloride, to prepare a solution in which trans-1,4-cyclohexane dicarboxylic acid dichloride and benzyltriethylammonium chloride were dissolved in CPME. This solution was referred to as acid chloride solution (H).

(Example 16) Preparation of a Solution in which Dicarboxylic Acid Chloride and Benzyltriethylammonium Chloride are Dissolved in Chloroform A similar operation to that of Example 15 was performed, except for changing the water-immiscible organic solvent from 86.5 g of CPME in Example 15 to 100 g of chloroform to prepare a solution in which trans-1,4-cyclohexane dicarboxylic acid dichloride and benzyltriethylammonium chloride were dissolved in chloroform. This solution was referred to as acid chloride solution (I).

(Example 17) Production of Mixture 11

A similar operation to that of Example 8 was performed, except for changing Example 8 by using the acid chloride solution (H) produced in Example 15 instead of the acid chloride solution (A) produced in Example 1. As a result, 15.22 g of a white solid was obtained. Confirming the composition with a similar method as for Example 8 revealed that 10.51 g (25.11 mmol) of the target monoester and 4.71 g (7.09 mmol) of diester were included.

(Example 18) Production of Mixture 12

A similar operation to that of Example 11 was performed, except for changing Example 11 by using the acid chloride solution (I) produced in Example 16 instead of the acid chloride solution (D) produced in Example 4. As a result, 15.36 g of a white solid was obtained. Confirming the composition with a similar method as for Example 11 revealed that 10.23 g (24.45 mmol) of the target monoester and 5.13 g (7.72 mmol) of diester were included.

(Comparative Example 1) Preparation of a Solution in which Dicarboxylic Acid Chloride and N,N-Dimethylformamide (DMF) are Dissolved in CPME To a 3-neck reaction vessel equipped with a thermometer, 8.65 g (50.2 mmol) of trans-1,4-cyclohexane dicarboxylic acid as the dicarboxylic acid compound (II), 86.5 g of CPME as a water-immiscible organic solvent, and 18 mg (0.25 mmol) of N,N-dimethylformamide as a reaction catalyst (activator) were added in a nitrogen stream. Subsequently, 12.54 g (105 mmol) of thionyl chloride as a halogenating agent was slowly added dropwise over 5 minutes at 23° C. After completion of the dropwise addition, the entire content was heated to 50° C. and was further stirred for 20 hours. After completion of the reaction, the result was concentrated with a rotary evaporator, and 80% (69 g) of the CPME that was used was extracted to prepare a solution in which trans-1,4-cyclohexane dicarboxylic acid dichloride and N,N-dimethylformamide were dissolved in CPME. This solution was referred to as acid chloride solution (α).

(Comparative Example 2) Preparation of a Solution in which Dicarboxylic Acid Chloride and N,N-Dimethylformamide are Dissolved in CPME A similar operation to that of Comparative Example 1 was performed, except for changing the 18 mg (0.25 mmol) of N,N-dimethylformamide in Comparative Example 1 to 367 mg (5.0 mmol) of N,N-dimethylformamide and changing the reaction time to five hours, to prepare a solution in which trans-1,4-cyclohexane dicarboxylic acid dichloride and N,N-dimethylformamide were dissolved in CPME. This solution was referred to as acid chloride solution (β).

(Comparative Example 3) Preparation of a Solution in which Dicarboxylic Acid Chloride and N,N-Dimethylformamide are Dissolved in Chloroform A similar operation to that of Comparative Example 2 was performed, except for changing the water-immiscible organic solvent from 86.5 g of CPME in Comparative Example 2 to 100 g of chloroform to prepare a solution in which trans-1,4-cyclohexane dicarboxylic acid dichloride and N,N-dimethylformamide were dissolved in chloroform. This solution was referred to as acid chloride solution (γ).

(Comparative Example 4) Production of Mixture 8

To a 3-neck reaction vessel equipped with a thermometer, the acid chloride solution (α) produced in Comparative Example 1 was added in a nitrogen stream, 235 g of CPME was then added, and the reaction vessel was immersed in an ice bath to achieve an internal temperature of 0° C. in the reaction solution. Then, 12.64 g (47.83 mmol) of 4-(6-acryloyloxy-hex-1-yloxy)phenol (produced by DKSH) as a hydroxy compound (IV) was added. Next, 5.08 g (50.2 mmol) of triethylamine as a base was slowly added dropwise over 5 minutes while maintaining the internal temperature of the reaction solution at 10° C. or lower. After completion of the dropwise addition, the entire content was further stirred for one hour at 0° C.

Next, 32 g of distilled water was added to the obtained reaction solution, the result was washed for 2 hours at 25° C., and the aqueous layer was then removed. The organic layer was washed three times with 53 g of a buffer solution (pH: 5.5) composed of an aqueous solution of a mixture of acetic acid and sodium acetate at a concentration of 1 mol/L, after which the buffer solution was extracted.

Subsequently, washing was performed once with 32 g of distilled water. To the obtained organic layer, 320 ml of n-hexane was added to cause crystals to precipitate, and the precipitated crystals were collected by filtration. After washing the obtained crystals with n-hexane, the crystals were vacuum dried, yielding 14.55 g of Mixture 8 as a white solid. Confirming the composition with a similar method as for Example 8 revealed that 9.81 g (23.45 mmol) of the target monoester and 4.73 g (7.12 mmol) of diester were included.

(Comparative Example 5) Production of Mixture 9

A similar operation to that of Comparative Example 4 was performed, except for changing Comparative Example 4 by using the acid chloride solution (β) produced in Comparative Example 2 instead of the acid chloride solution (α) produced in Comparative Example 1 and by changing the 5.08 g (50.2 mmol) of triethylamine to 6.10 g (60.2 mmol) of triethylamine. As a result, 11.47 g of a white solid was obtained. Confirming the composition with a similar method as for Example 8 revealed that 7.51 g (17.95 mmol) of the target monoester and 3.96 g (5.96 mmol) of diester were included.

(Comparative Example 6) Production of Mixture 10

A similar operation to that of Comparative Example 4 was performed, except for changing Comparative Example 4 by using the acid chloride solution (γ) produced in Comparative Example 3 instead of the acid chloride solution (α) produced in Comparative Example 1, by using chloroform instead of CPME, and by changing the 5.08 g (50.2 mmol) of triethylamine to 6.10 g (60.2 mmol) of triethylamine. As a result, 11.35 g of a white solid was obtained. Confirming the composition with a similar method as for Example 8 revealed that 7.41 g (17.71 mmol) of the target monoester and 3.94 g (5.93 mmol) of diester were included.

The above results are summarized in Tables 1 and 2.

In the Tables, the "activator" refers to the reaction catalyst for the acid chloridization reaction to form acid chloride, the "added amount of activator" refers to the ratio (mol ratio) with respect to the amount of the dicarboxylic acid compound, and the "reaction solvent" refers to the water-immiscible organic solvent. The "Acid chl. sol." is an abbreviation for "Acid chloride solution".

TABLE 1

| | | Acid chloridization reaction | | | | | | |
|---|---|---|---|---|---|---|---|---|
| | | Activator | | | Acid | | | |
| | | Type | Added amount (eq.) | Reaction solvent | chl. sol. | Temperature (° C.) | Time (hours) | Conversion rate (%) |
| Example 1 | | benzyltrimethylammonium chloride | 0.005 | CPME | A | 50 | 1 | 99.7 |
| Example 2 | | tri(n-octyl)methylammonium chloride (product name: Aliquat) | 0.005 | CPME | B | 50 | 1 | 99.8 |
| Example 3 | | trioctylmethylammonium chloride mixture (product name: Adogen) | 0.005 | CPME | C | 50 | 1 | 99.4 |
| Example 4 | | benzyltrimethylammonium chloride | 0.005 | chloroform | D | 50 | 1 | 99.5 |
| Example 5 | | tri(n-octyl)methylammonium chloride (product name: Aliquat) | 0.005 | chloroform | E | 50 | 1 | 99.2 |
| Example 6 | | trioctylmethylammonium chloride mixture (product name: Adogen) | 0.005 | chloroform | F | 50 | 1 | 99.5 |
| Example 7 | | tri(n-octyl)methylammonium chloride (product name: Aliquat) | 0.100 | CPME | G | 50 | 0.5 | 99.8 |
| Example 15 | | benzyltriethylammonium chloride | 0.005 | CPME | H | 50 | 1 | 99.6 |
| Example 16 | | benzyltriethylammonium chloride | 0.005 | chloroform | I | 50 | 1 | 99.7 |
| Comparative Example 1 | | N,N-dimethylformamide | 0.005 | CPME | α | 50 | 20 | 95.5 |
| Comparative Example 2 | | N,N-dimethylformamide | 0.100 | CPME | β | 50 | 5 | 98.6 |
| Comparative Example 3 | | N,N-dimethylformamide | 0.100 | chloroform | γ | 50 | 5 | 97.9 |

TABLE 2

| | | Esterification reaction | | | | |
|---|---|---|---|---|---|---|
| | Acid | | | | Reaction performance | |
| | chl. sol. used | Acquired amount of mixture (g) | | | Reaction conversion rate (%) | Monoester content*[1] (wt %) |
| | | Monoester | Diester | Sum | | |
| Example 8 | A | 10.55 | 4.67 | 15.22 | 98.3% | 69.35% |
| Example 9 | B | 10.69 | 4.76 | 15.45 | 98.8% | 69.17% |
| Example 10 | C | 10.31 | 4.62 | 14.93 | 98.5% | 69.03% |
| Example 11 | D | 10.20 | 5.14 | 15.34 | 99.0% | 66.47% |
| Example 12 | E | 10.21 | 5.20 | 15.41 | 98.8% | 66.25% |
| Example 13 | F | 10.34 | 5.17 | 15.51 | 98.4% | 66.65% |
| Example 14 | G | 10.35 | 4.79 | 15.14 | 98.8% | 68.35% |
| Example 17 | H | 10.51 | 4.71 | 15.22 | 98.9% | 69.05% |
| Example 18 | I | 10.23 | 5.13 | 15.36 | 98.6% | 66.60% |
| Comparative Example 4 | α | 9.81 | 4.73 | 14.55 | 97.9% | 67.47% |
| Comparative Example 5 | β | 7.51 | 3.96 | 11.47 | 82.5% | 65.47% |
| Comparative Example 6 | γ | 7.41 | 3.94 | 11.35 | 83.1% | 65.31% |

*[1]Calculated from HPLC calibration curve

From Table 1, it is clear that by performing an acid chloridization reaction in the presence of a tetraalkylammonium salt, the reaction progresses faster with a small added amount and is more efficient than in the case of using conventionally known N,N-dimethylformamide.

Furthermore, Table 2 shows that even in the esterification reaction of a subsequent step, an acid chloride solution produced using a tetraalkylammonium salt provides good reaction performance, whereas when using an acid chloride solution produced using N,N-dimethylformamide, the conversion rate lowers and the reaction is not completed. Moreover, the yield tends to reduce. This is caused by the common generation of by-products in the reaction system.

(Measurement Example 1) Measurement of Amount of Hydrochloric Acid Gas in Solution in which Dicarboxylic Acid Chloride and Benzyltrimethylammonium Chloride are Dissolved in CPME (Before Concentration)

To a 3-neck reaction vessel equipped with a thermometer, 8.65 g (50.2 mmol) of trans-1,4-cyclohexane dicarboxylic acid as the dicarboxylic acid compound (II) and 86.5 g of CPME as a water-immiscible organic solvent were added in a nitrogen stream. Then, 47 mg (0.25 mmol) of benzyltrimethylammonium chloride as the tetraalkylammonium salt (I) was added. Subsequently, 12.54 g (105 mmol) of thionyl chloride as a halogenating agent was slowly added dropwise over 5 minutes at 23° C. After completion of the dropwise addition, the entire content was heated to 50° C. and was further stirred for one hour. After completion of the reaction, 16 g (500 mmol) of methanol was added, and the result was stirred for one hour. Subsequently, the content of hydrochloric acid gas was measured by titration using sodium hydroxide, revealing that 25.5 parts by mass of hydrochloric acid gas remained per 100 parts by mass of the generated trans-1,4-cyclohexane dicarboxylic acid dichloride.

(Measurement Example 2) Measurement of Amount of Hydrochloric Acid Gas in Solution in which Dicarboxylic Acid Chloride and Benzyltrimethylammonium Chloride are Dissolved in CPME (after Concentration)

To a 3-neck reaction vessel equipped with a thermometer, 8.65 g (50.2 mmol) of trans-1,4-cyclohexane dicarboxylic acid as the dicarboxylic acid compound (II) and 86.5 g of CPME as a water-immiscible organic solvent were added in a nitrogen stream. Then, 47 mg (0.25 mmol) of benzyltrimethylammonium chloride as the tetraalkylammonium salt (I) was added. Subsequently, 12.54 g (105 mmol) of thionyl chloride as a halogenating agent was slowly added dropwise over 5 minutes at 23° C. After completion of the dropwise addition, the entire content was heated to 50° C. and was further stirred for one hour. After completion of the reaction, the result was concentrated with a rotary evaporator, and 80% (69 g) of the CPME that was used was extracted to prepare a solution in which trans-1,4-cyclohexane dicarboxylic acid dichloride and benzyltrimethylammonium chloride were dissolved in CPME. This solution was referred to as acid chloride solution (A). Next, 16 g (500 mmol) of methanol was added to the acid chloride solution (A), and the result was stirred for one hour. Subsequently, the content of hydrochloric acid gas was measured by titration using sodium hydroxide, revealing that 1.8 parts by mass of hydrochloric acid gas remained per 100 parts by mass of the generated trans-1,4-cyclohexane dicarboxylic acid dichloride.

The invention claimed is:

1. A method for producing a monoester compound indicated by Formula (V) below,

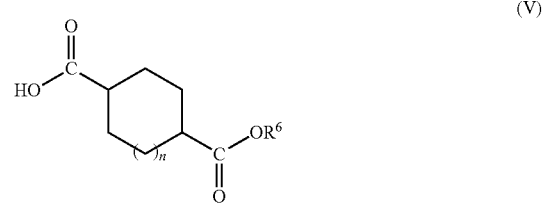

(V)

where in Formula (V), $R^6$ represents an organic group and n represents 0 or 1, the method comprising:

a step α of reacting a halogenating agent and a dicarboxylic acid compound represented by Formula (II) below in a water-immiscible organic solvent in the presence of a tetraalkylammonium salt represented by Formula (I) below to obtain a water-immiscible organic solvent solution including an acid halide compound represented by Formula (III) below,

$R^1R^2R^3R^4N^+A^-$         (I)

where in Formula (I), $A^-$ represents a halide ion or $R^5SO_3^-$, $R^5$ represents a methyl group, a phenyl group, or a 4-methyl phenyl group, $R^1$, $R^2$, $R^3$, and $R^4$ independently represent an alkyl group that is unsubstituted or has a substituent, and a total number of carbon atoms in $R^1$, $R^2$, $R^3$, and $R^4$ is at least 4 and no greater than 100,

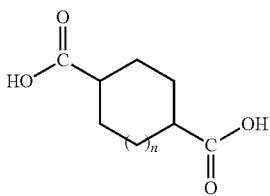

where in Formula (II), n represents 0 or 1,

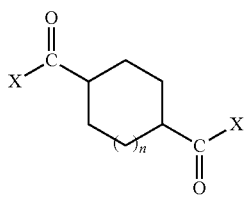

where in Formula (III), n represents 0 or 1, and X represents a halogen atom; and
a step β of concentrating the obtained water-immiscible organic solvent solution to obtain an acid halide solution,
a step γ of adding a base and a hydroxy compound indicated by Formula (IV), $R^6OH$, where in Formula (IV), $R^6$ represents the organic group, to the acid halide solution, and wherein the water-immiscible organic solvent is an organic solvent having a solubility of no greater than 10 g/L in water at 25° C.

2. The method for producing a monoester compound of claim 1, wherein the hydroxy compound indicated by Formula (IV) is a compound indicated by Formula (IV-1) below,

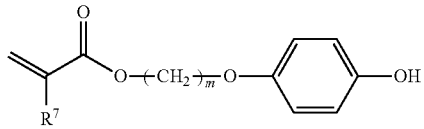

where in Formula (IV-1), $R^7$ represents a hydrogen atom, a methyl group, or a chlorine atom, and m is an integer of at least 1 and no greater than 20.

3. The method for producing a monoester compound of claim 1, further comprising a step δ, after the step γ, of washing a reaction solution obtained in the step γ with a weakly acidic buffer solution.

4. The method for producing a monoester compound of claim 3, wherein the weakly acidic buffer solution is an aqueous solution with a pH of at least 5.0 and no greater than 6.0.

5. The method for producing a monoester compound of claim 3, wherein the weakly acidic buffer solution is an aqueous solution of a mixture of acetic acid and sodium acetate and/or an aqueous solution of a mixture of potassium hydrogen phthalate and sodium hydroxide.

6. The method for producing a monoester compound of claim 1, wherein the halogenating agent is at least one selected from the group consisting of thionyl chloride, oxalyl chloride, sulfuryl chloride, phosphoryl chloride, phosphorus trichloride, and phosphorus pentachloride.

7. The method for producing a monoester compound of claim 1, wherein the tetraalkylammonium salt is at least one selected from the group consisting of benzyltrimethylammonium chloride, benzyltriethylammonium chloride, methyltrioctylammonium chloride, and tetrabutylammonium chloride.

8. The method for producing a monoester compound of claim 1, wherein the dicarboxylic acid compound represented by Formula (II) is a compound indicated by Formula (II-a) below,

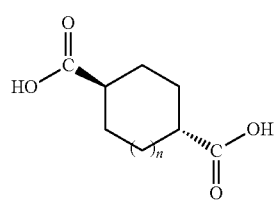

where in Formula (II-a), n represents 0 or 1.

* * * * *